United States Patent
Kado

(10) Patent No.: US 10,543,176 B2
(45) Date of Patent: Jan. 28, 2020

(54) TOPICAL FORMULATION FOR BINDING TO DERMATOLOGICAL CANNABINOID RECEPTORS

(71) Applicant: Jessica Kado, West Bloomfield, MI (US)

(72) Inventor: Jessica Kado, West Bloomfield, MI (US)

( * ) Notice: Subject to any disclaimer, the term of this patent is extended or adjusted under 35 U.S.C. 154(b) by 0 days.

(21) Appl. No.: 15/627,745

(22) Filed: Jun. 20, 2017

(65) Prior Publication Data

US 2018/0360770 A1 Dec. 20, 2018

(51) Int. Cl.
| | |
|---|---|
| *A61K 36/53* | (2006.01) |
| *A61K 31/015* | (2006.01) |
| *A61K 9/00* | (2006.01) |
| *A61K 9/06* | (2006.01) |
| *A61K 31/01* | (2006.01) |
| *A61K 36/61* | (2006.01) |
| *A61K 36/185* | (2006.01) |
| *A61K 36/752* | (2006.01) |
| *A61K 36/86* | (2006.01) |
| *A61K 36/28* | (2006.01) |
| *A61K 31/164* | (2006.01) |
| *A61K 36/484* | (2006.01) |
| *A61K 36/736* | (2006.01) |
| *A61K 47/10* | (2017.01) |
| *A61K 47/14* | (2017.01) |
| *A61K 36/286* | (2006.01) |
| *A61K 31/355* | (2006.01) |
| *A61K 36/54* | (2006.01) |
| *A61K 36/899* | (2006.01) |
| *A61K 31/07* | (2006.01) |
| *A61K 31/593* | (2006.01) |
| *A61K 47/26* | (2006.01) |
| *A61K 47/18* | (2017.01) |
| *A61K 47/32* | (2006.01) |
| *A61K 31/661* | (2006.01) |
| *A61K 31/575* | (2006.01) |

(52) U.S. Cl.
CPC .......... *A61K 31/015* (2013.01); *A61K 9/0014* (2013.01); *A61K 9/06* (2013.01); *A61K 31/01* (2013.01); *A61K 31/07* (2013.01); *A61K 31/164* (2013.01); *A61K 31/355* (2013.01); *A61K 31/575* (2013.01); *A61K 31/593* (2013.01); *A61K 31/661* (2013.01); *A61K 36/185* (2013.01); *A61K 36/28* (2013.01); *A61K 36/286* (2013.01); *A61K 36/484* (2013.01); *A61K 36/53* (2013.01); *A61K 36/54* (2013.01); *A61K 36/61* (2013.01); *A61K 36/736* (2013.01); *A61K 36/752* (2013.01); *A61K 36/86* (2013.01); *A61K 36/899* (2013.01); *A61K 47/10* (2013.01); *A61K 47/14* (2013.01); *A61K 47/18* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 9,526,752 | B1 * | 12/2016 | Lowe | A61K 36/185 |
| 2010/0216785 | A1 * | 8/2010 | Lazzari | A61K 9/1075 |
| | | | | 514/232.8 |
| 2014/0302121 | A1 * | 10/2014 | Bevier | A61K 47/10 |
| | | | | 424/450 |
| 2016/0220623 | A1 * | 8/2016 | Florence | A61K 31/401 |
| 2018/0042890 | A1 * | 2/2018 | Sinai | A61K 31/352 |

FOREIGN PATENT DOCUMENTS

WO WO 2017/149392 * 9/2017

* cited by examiner

*Primary Examiner* — Ralph J Gitomer
(74) *Attorney, Agent, or Firm* — Fitch, Even, Tabin & Flannery, LLP

(57) ABSTRACT

A topical cream or ointment is provided that provides for the binding to CB1 and/or CB2 receptors for the soothing of dermatological itching. The cream or ointment composition provides the effect of cannabinoids without the actual use of cannabinoids. Several essential oils, including Black Pepper, Ylang Ylang, and Melissa essential oils in combination, contain caryophyllene, a sesquiterpene, in effective amounts to bind to the CB2 receptor and help reduce an urge to itch the skin.

1 Claim, No Drawings

TOPICAL FORMULATION FOR BINDING TO DERMATOLOGICAL CANNABINOID RECEPTORS

RELATED APPLICATIONS

There are no previously filed, nor currently any co-pending applications, anywhere in the world.

BACKGROUND OF THE INVENTION

1. Field of the Invention

The present invention is relevant to the field of suppressing sensory afferent neuron symptoms of itch and, more particularly, to itch suppression through the binding of agents to dermatological cannabinoid receptors and compositions for the same.

2. Description of the Related Art

Most recently, research into the topical use of cannabinoids has found therapeutic dermatological effects of such compounds. Numerous studies have investigated medical uses of cannabinoids for chronic pain, spacticity, anorexia and nausea. Topical therapeutic uses have further been found for the treatment of dermatological conditions including pruritus, inflammatory skin diseases and skin cancer.

Such recent findings indicate cannabidiol (CBD) and cannabigerol (CBG) bind to Cannabinoid Receptor Type 1 (CB1) and/or Cannabinoid Receptor Type 2 (CB2) receptors, resulting in therapeutic effects in treating psoriasis, pruitus, allergic contact dermatitis, atopic dermatitis and other eczematous dermatoses. In light of such recent knowledge, persons having ordinary skill in the relevant art may use cannabinoids to stimulate or to bind to cannabinoid receptors in the skin in order to excite or prevent a response and, in particular, to prevent itching.

Receptors throughout the body that are part of the endocannabinoid system are known to be involved in a variety of physiological processes. However, while cannabinoids are currently allowed in twenty eight states for medical applications, currently exist some insurmountable barriers to reliance of synthetic or process products of medical marijuana in the treatment of dermatological itch. These include, inter alia, lack of availability in 22 states; heightened regulatory scrutiny and its impact on the supply chain; requirement of doctor prescription and supervision; non-medical 'political' negative reactions to use of a cannabis related product; and, most significantly, the costs associated with the inclusion of cannabanoid products into a topical formulation. Both the use of cannabis related ingredients and such cost are especially barriers in the creation of an over-the-counter topical agent.

Consequently, a need exists for the use of binding to CB1 and/or CB2 receptors in a topical ointment in the soothing of dermatological itching. A further need exists for such a topical ointment that emulates the use of cannabinoid without the actual use of cannabinoids.

SUMMARY OF THE INVENTION

Aspects of the invention are summarized below to aid in the understanding of embodiments of the invention and the application. Yet, the invention is fully defined by the claims of the applications.

It is thus an object of the present invention to provide a topical ointment for the treatment of dermatological itching through binding to the CB1 and/or CB2 receptors.

It is a further object of the present invention to provide for CB1 and/or CB2 receptor bindings without the use of cannabinoid ingredients.

It is a feature of the present invention to provide a topical cream or ointment that utilizes a blend of aromatics and essential oils in a proportion and amount that emulates the use of cannabinoids, and at a commercially effective cost.

The present invention provides a topical formulation for binding to dermatological cannabinoid receptors. Essential oil extracts are provided and blended in a proportion such as to create a phyto-pseudo-cannabinoid formulation. The phyto-pseudo-cannabis formulation comprises extracts of sweet almond, safflower, vitamin E, chamomile, Avocado, lavender, lemon balm, vitamin A, Vitamin D, corn, pansy (viola tricolor) clove, rosemary, yarrow, and ylang ylang. These leaf, flower and herb oils and extracts are provided in a proportion and in small amounts and with binders and stabilizers. Though such natural extracts can generally each be expensive to obtain, the use of the combination allows for such relatively small amounts to be effective and to allow for the finished topical cream or ointment to be inexpensive enough to allow for competitive commercial applications. Further, the ingredients themselves at the levels provided are each generally considered safe and, as such, a finished topical cream or ointment should be viable for over-the-counter sales.

Further features of the invention will become apparent in the course of the following detailed description.

DESCRIPTION OF THE PREFERRED EMBODIMENTS

It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Cannabinoid receptors are of a class of cell membrane receptors under the G protein-coupled receptor superfamily. Cannabinoid receptors are known to be activated by three major groups of ligands: endocannabinoids, produced by the mammillary body; plant cannabinoids (such as Cannabidiol, produced by the cannabis plant); and synthetic cannabinoids (such as HU-210). All of the endocannabinoids and plant cannabinoids are lipophilic, such as fat soluble compounds.

In providing a topical medicament for the treatment of dermatological itch, a composition that provides for binding to CB1 and/or CB2 receptors have been found to be effective. It has been found that the use of a composition of plant extracts can mimic the endocannabinoids and plant cannabinoids binding to CB1 and/or CB2 receptors, and that such receptor occupancy can diminish a dermatological itch sensation.

According to one aspect of the present invention the topical preparation is provided as a topical cream or ointment that utilizes a blend of aromatics and essential oils in a proportion and amount that emulates this CB1 and/or CB2 receptor binding. Essential oil extracts are provided and blended in a proportion such as to create a phyto-pseudo-cannabinoid formulation. Most suitably the formulation contains the following:

| % wt | Ingredient |
| --- | --- |
| 0.70 | Essential Oil Blend (comprised of Clove Oil, Lavender Oil, Rosemary Oil, Ylang Ylang Oil, and Lemon Oil) |
| 0-1 | Additional Lavender |
| 0-1 | Additional Lemon Extract |
| 1.5 | Pansy (Viola Tricolor) Extract |
| 0-1 | Chamomile Flower Extract |
| >1 | Ceramides |
| >1 | Licorice Root |
| >1 | Yarrow |

Caryophyllene is a sesquiterpene found in high amounts of several Essential Oils, including Black Pepper, Ylang Ylang, and Melissa essential oils. It activates a CB2 receptors with psychoactive activity. The essential oil blend that includes the five listed essential oils all include some level of caryophyllene to bind to the CB2 receptor and help reduce an urge to itch your skin.

According to another aspect of the present invention topical cream or ointment formulation may contain the following: sweet almond; safflower; vitamin E; chamomile; Avocado; lavender; lemon balm; vitamin A; Vitamin D; corn; pansy (viola tricolor) clove; rosemary; yarrow; and ylang ylang. These leaf, flower and herb oils and extracts are provided in a proportion and in small amounts and with binders and stabilizers. Though such natural extracts can generally each be expensive to obtain, the use of the combination allows for such relatively small amounts to be used overall such as to allow for the finished topical cream or ointment to be inexpensive enough to allow for competitive commercial applications.

According to yet another aspect of the present invention, including binders and stabilizers, the topical cream or ointment formulation may contain the following: Water, Prunus Amygdalus Dulcis (Sweet Almond) Oil, Glycerin, Isopropyl Palmitate, Carthamus Tinctorius (Safflower) Seed Oil, Stearic Acid, Tocopheryl (Vitamin E) Acetate, Glyceryl Stearate SE, Persea Gratissima (Avocado) Oil, Chamomilla Recutitia (Chamomile) Flower Extract, Lavandula Angustifolia (Lavender) Flower Extract, Melissa Officinalis (Lemon Balm) Leaf Extract, Tocopherol (Vitamin E), Zea Mays (Corn) Oil, Retinyl Palmitate (Vitamin A), Cholecalciferol (Vitamin D), Polysorbate 80, Cetyl Alcohol, Aminomethyl Propanol, Sorbitan Oleate, Carbomer, Tetrasodium Glutamate Diacetate, Pansy (Viola Tricolor) Extract, Polyacrylate-13, Polyisobutene, Polysorbate 20, Eugenia Caryophyllus (Clove) Flower Oil, Lavandin Grosso (Lavender) Oil, Rosmarinus Officinalis (Rosemary) Leaf Oil, Canaga Odorata (Ylang Ylang) Flower Oil, Melissa Officinalis (Lemon Balm) Leaf Oil, Dipotassium Glycyrrhizinate, Achillea Millefolium (Yarrow) Flower Extract, Ceramide 3, Ceramide 6 II, Ceramide 1, Phytosphingosine, Cholesterol, Sodium Lauroyl Lactylate, Carbomer, Xanthan Gum, Phenoxyethanol Ethylhexyl Glycerin.

According to still a final aspect of the present invention, the topical cream or ointment formulation may contain the following:

| % wt | Ingredient |
| --- | --- |
| | Water |
| | Prunus Amygdalus Dulcis (Sweet Almond) Oil |
| | Glycerin |
| | Isopropyl Palmitate |
| | Carthamus Tinctorius (Safflower) Seed Oil |
| | Stearic Acid |
| | Tocopheryl (Vitamin E) Acetate |
| | Glyceryl Stearate SE |
| | Persea Gratissima (Avocado) Oil |
| | Chamomilla Recutitia (Chamomile) Flower Extract |
| | Lavandula Angustifolia (Lavender) Flower Extract |
| | Melissa Officinalis (Lemon Balm) Leaf Extract |
| | Tocopherol (Vitamin E) |
| | Zea Mays (Corn) Oil |
| | Retinyl Palmitate (Vitamin A) |
| | Cholecalciferol (Vitamin D) |
| | Polysorbate 80 |
| | Cetyl Alcohol |
| | Aminomethyl Propanol |
| | Sorbitan Oleate |
| | Carbomer |
| | Tetrasodium Glutamate Diacetate |
| | Pansy (Viola Tricolor) Extract |
| | Polyacrylate-13 |
| | Polyisobutene |
| | Polysorbate 20 |
| | Eugenia Caryophyllus (Clove) Flower Oil |
| | Lavandin Grosso (Lavender) Oil |
| | Rosmarinus Officinalis (Rosemary) Leaf Oil |
| | Canaga Odorata (Ylang Ylang) Flower Oil |
| | Melissa Officinalis (Lemon Balm) Leaf Oil |
| | Dipotassium Glycyrrhizinate |
| | Achillea Millefolium (Yarrow) Flower Extract |
| | Ceramide 3 |
| | Ceramide 6 II |
| | Ceramide 1 |
| | Phytosphingosine |
| | Cholesterol |
| | Sodium Lauroyl Lactylate |
| | Carbomer |
| | Xanthan Gum |
| | Phenoxyethanol Ethylhexyl Glycerin. |

These ingredients composition of the present inventions provides a new and surprising synergistic effect.

2. Operation of the Preferred Embodiment

In operation, a topical cream or ointment is provided that provides for the binding to CB1 and/or CB2 receptors for the soothing of dermatological itching. The cream or ointment composition provides the effect of cannabinoid without the actual use of cannabinoids. Several essential oils, including Black Pepper, Ylang Ylang, and Melissa essential oils in combination, contain caryophyllene, a sesquiterpene, in effective amounts to bind to the CB2 receptor and help reduce an urge to itch the skin.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims.

In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of Warner-Jenkinson Company, v. Hilton Davis Chemical, 520 US 17 (1997) or Festo Corp. v. Shoketsu Kinzoku Kogyo Kabushiki Co., 535 U.S. 722 (2002), or other similar caselaw or subsequent precedent should not be made if any future claims are added or amended subsequent to this Provisional Patent Application.

What is claimed is:

1. A topical cream for treatment of a dermatological itch, comprising:
   0.70% wt of an Essential Oil Blend comprising a composition of Clove Oil, Lavender Oil, Rosemary Oil, Ylang Ylang Oil, and Lemon Oil;
   0.1-1% wt Lavender;
   0.1-1% wt Lemon Extract;
   1.5% wt Pansy (Viola Tricolor) Extract;
   0.1-1% wt Chamomile Flower Extract;
   >1% wt Ceramides;
   >1% wt Licorice Root; and
   >1% wt Yarrow.

* * * * *